(12) United States Patent
Min et al.

(10) Patent No.: US 11,504,439 B2
(45) Date of Patent: Nov. 22, 2022

(54) RADIOACTIVE COMPOUND FOR DIAGNOSIS OF MALIGNANT MELANOMA AND USE THEREOF

(71) Applicant: INDUSTRY FOUNDATION OF CHONNAM NATIONAL UNIVERSITY, Gwangju (KR)

(72) Inventors: Jung-Joon Min, Gyeonggi-do (KR); Dong-Yeon Kim, Gwangju (KR); Ayoung Pyo, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 16/511,079

(22) Filed: Jul. 15, 2019

(65) Prior Publication Data
US 2019/0336621 A1 Nov. 7, 2019

Related U.S. Application Data

(63) Continuation-in-part of application No. PCT/KR2018/000549, filed on Jan. 11, 2018.

(30) Foreign Application Priority Data

Jan. 13, 2017 (KR) .......................... 10-2017-0006088

(51) Int. Cl.
*A61K 51/00* (2006.01)
*A61M 36/14* (2006.01)
*A61K 51/04* (2006.01)

(52) U.S. Cl.
CPC .......... *A61K 51/0455* (2013.01); *A61K 51/04* (2013.01); *A61K 51/048* (2013.01); *A61K 51/0474* (2013.01); *A61K 51/0482* (2013.01); *A61K 51/0485* (2013.01)

(58) Field of Classification Search
CPC ................ A61K 51/0455; A61K 51/04; A61K 51/0474; A61K 51/048; A61K 51/0482; A61K 51/0485
USPC ....................................................... 424/1.89
See application file for complete search history.

(56) References Cited

U.S. PATENT DOCUMENTS

2015/0023877 A1* 1/2015 Bu ..................... A61K 51/0455
424/1.89

OTHER PUBLICATIONS

Kim et al. Bioorg. Med. Chem. 2012, 4915-4920. (Year: 2012).*
Greguric et al. J. Med. Chem. 2009, 52, 5299-5309.*
Ren, et al. "Melanin-Targeted Preclinical PET Imaging of Melanoma Metastasis" The Journal of Nuclear Medicine • vol. 50 • No. 10 • Oct. 2009, pp. 1692-1699.
Nicholl, et al. "Pharmacokinetics of Iodine-123-IMBA for Melanoma Imaging" The Journal of Nuclear Medicine, vol. 38, No. 1, Jan. 1997, pp. 128-133.
Moreau, et al. "Synthesis, Radiolabeling, and Preliminary Evaluation in Mice of Some (N-Diethylaminoethyl)-4-Iodobenzamide Derivatives as Melanoma Imaging Agents" Nucl. Med. Biol. vol. 22, No. 6, pp. 737-747, 1995.
Moins, et al. "Synthesis, characterization and comparative biodistribution study of a new series of p-Iodine-125 benzamides as potential melanoma imaging agents" Nuclear Medicine and Biology 28 (2001) 799-808.
Liu et al., "Development of 18F-Labeled Picolinamide Probes for PET Imaging of Malignant Melanoma" J. Med. Chem. 2013, 56, 895-901.
Labarre, et al "Evaluation in mice of some iodinated melanoma imaging agents using cryosectioning and multi-wire proportional counting" European Journal of Nuclear Medicine vol. 26, No. 5, May 1999. pp. 494-498.
Dittmann, "In Vitro Studies on the Cellular Uptake of Melanoma Imaging Aminoalkyl—Iodobenzamide Derivatives (ABA)" Nuclear Medicine & Biology, vol. 26, pp. 51-56, 1999.
Brandau, et al. "Structure Distribution Relationship of Iodine-123-Iodobenzamides as Tracers for the Detection of Melanotic Melanoma" The Journal of Nuclear Medicine, vol. 37, No. 11, Nov. 1996 pp. 1865-1871.
Billaud, "Development and Preliminary Evaluation of TFIB, a New Bimodal Prosthetic Group for Bioactive Molecule Labeling" ACS Med. Chem. Lett. 2015, 6, 168-172.
Ayoung Pyo, et al. "Ultrasensitive detection of malignant melanoma using PET molecular imaging probes" PNAS | Jun. 9, 2020, vol. 117, No. 23, pp. 12991-12999.

* cited by examiner

*Primary Examiner* — Michael G. Hartley
*Assistant Examiner* — Sean R Donohue
(74) *Attorney, Agent, or Firm* — Stuart H. Mayer; Mayer & Wiliams PC

(57) ABSTRACT

The present invention provides a novel radioactive compound for imaging malignant melanoma and a use thereof as a contrast agent for PET imaging.

3 Claims, 9 Drawing Sheets

RADIOACTIVE COMPOUND FOR DIAGNOSIS OF MALIGNANT MELANOMA AND USE THEREOF

TECHNICAL FIELD

The present invention relates to a novel compound and use thereof, and more particularly to a novel radioactive compound for PET imaging and use thereof.

BACKGROUND

Malignant melanoma is known as one of the deadliest cancers due to its high systemic metastatic potential. Malignant melanoma accounts for about 5% of all skin cancers, but it accounts for more than 50% of skin cancer-related deaths. Moreover, the incidence of the disease has doubled over the past two decades and is steadily increasing. To date, effective therapeutic agents for melanoma have not been developed. However, early diagnosis and precise determination of stage of disease are presented as important approaches to improve the survival rate of patients with malignant melanoma.

Positron-emission tomography (PET), which is also called positron tomography, is one of the functional imaging techniques used in the nuclear medicine department and it is one of the nuclear medicine diagnosis methods using positron emission, which is performed by injecting a drug with a radioactive isotope into the body and then tracking and determining its distribution in the by using a positron emission tomography device. Through PET, it is possible to obtain a receptor imaging or a metabolic imaging for the diagnosis of cancer, heart diseases, and brain diseases, and furthermore for brain function evaluation. A positron has a physical property similar to that of an electron having a negative charge, but has a positive charge. These positions are a type of radiation emitted by radioactive isotopes such as $^{11}C$, $^{13}N$, $^{15}O$, and $^{18}F$. These elements are the main constituents of living organisms and can be used to make medicines. F-18-fluoro-deoxyglucose (F-18-FDG), which is the most commonly used radiopharmaceutical, is a glucose-like substance, and it is injected into the living body, it accumulates much in areas where glucose metabolism is enhanced like cancer.

Recently, a Positron Emission Tomography/Computed Tomography (PET/CT) scanner combining a positron emission tomography scanner and a computed tomography (CT) scanner is widely used. PET/CT has better image quality than conventional positron emission tomography because it provides anatomical information and more accurate image correction due to the addition of a computed tomography scanner.

In addition to the above F-18-FDG, several PET probes such as 6-$^{18}$F-Fluoro-L-dihydroxyphenylalanine ($^{18}$F-DOPA), L-[methyl-$^{11}$C]methionien ($^{11}$C-methionine), 3'-$^{18}$F-fluoro-3'-deoxy-L-thymidine ($^{18}$F-FLT), $^{18}$F-galacto-RGD peptide were tested for melanoma patients. However, the detection rate of these probe molecules for melanoma was extremely low. $^{18}$F-FDG, a cancer detection probe, also failed to identify metastatic foci with less than 1 cm in diameter in the lung, liver, and brain, which are the major metastatic foci to which melanoma spreads.

Recently, $^{18}$F—N-[2-(diethyl amino) ethyl]-4-fluoro-benzamide ($^{18}$F-FBZA) has been developed and reported as a contrast agent for PET targeting melanin for the detection of metastatic melanoma (Ren et al., *J. Nucl. Med.* 50(10): 1692-1699, 2009).

Technical Problems

However, although the above-described PET radioactive compounds for detecting melanoma has the principle of inducing selective intake them by melanoma using the chemical conversion of benzamide structure, they have the problem of low intake rate to melanoma and poor image quality and thus there is a demand for improvement for these problems.

Accordingly, the present invention has been made to solve the above-mentioned problems, and it is an object of the present invention to provide a novel PET imaging radioactive compound having improved melanoma targeting ability.

It is another object of the present invention to provide various uses of the above-mentioned compounds such as a PET contrast agent containing the compound.

However, these problems are exemplary and do not limit the scope of the present invention.

Technical Solutions

In an aspect of the present invention, there is provided a novel radioactive compound or a pharmaceutically acceptable salt thereof having the following formula:

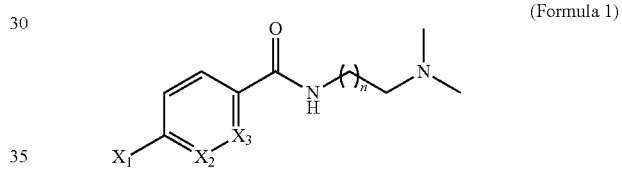

(Formula 1)

wherein, $X_1$ is a radioactive isotope halogen element selected from the group consisting of $^{18}$F, $^{76}$Br, $^{123}$I, $^{124}$I and $^{131}$I, or a complex of a chelator and a radioactive metal or a salt thereof selected from the group consisting of $^{68}$Ga, Al$^{18}$F, $^{62}$Cu and $^{64}$Cu; $X_2$ and $X_3$ are independently C or N; and n is an integer from 1 to 5.

In another aspect of the present invention, there is provided a contrast agent for positron emission tomography (PET) comprising the compound of formula (1) or an acceptable salt thereof as an active ingredient.

In another aspect of the present invention, there is provided a method for diagnosing melanoma of a subject comprising administering the above-mentioned radioactive compound to the subject.

Effect of the Invention

The novel radioactive compounds and pharmaceutically acceptable salts thereof according to one embodiment of the present invention can be used as PET contrast agents. The radioactive compound according to one embodiment of the present invention has an advantage that the targeting ability to melanoma is improved and the metastasis of melanoma can be also detected clearly. However, the scope of the present invention is not limited by the above effects.

DETAILED DESCRIPTION OF EMBODIMENTS

Figure 1:
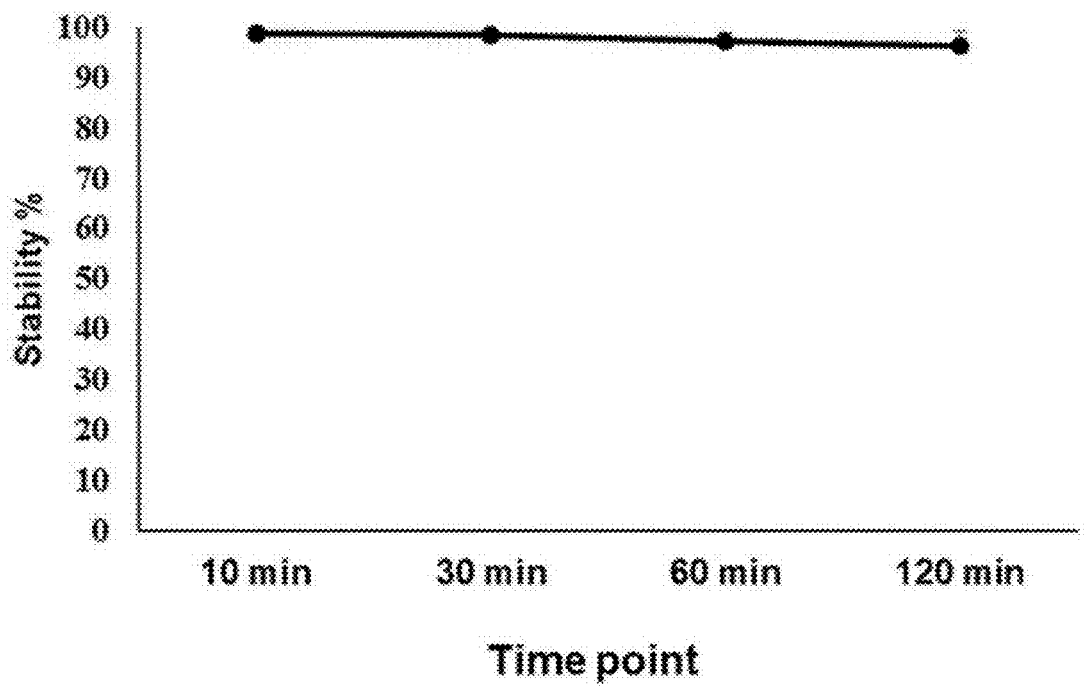
FIG. 1 is a graph showing the results of confirming the stability of [$^{18}$F]DMFB according to an embodiment of the present invention.

In an aspect of the present invention, there is provided a novel radioactive compound or a pharmaceutically acceptable salt thereof having the following formula:

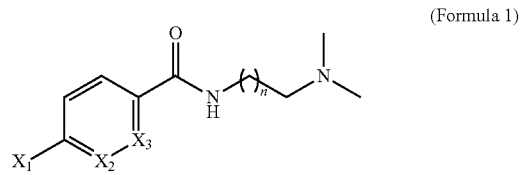

(Formula 1)

wherein, $X_1$ is a radioactive isotope halogen element selected from the group consisting of $^{18}$F, $^{76}$Br, $^{123}$I, $^{124}$I and $^{131}$I, or a complex of a chelator and a radioactive metal or a salt thereof selected from the group consisting of $^{68}$Ga, Al$^{18}$F, $^{62}$Cu and $^{64}$Cu; $X_2$ and $X_3$ are independently C or N; and n is an integer from 1 to 5.

According to the radioactive compound or a pharmaceutically acceptable salt, the chelator may be one selected from the group consisting of NOTA (1,4,7-triazacyclononane-N, N'-tetraazacyclododecane-1,4,7,10-tetraacetic acid), di(t-Bu)-NOTA, NOTA-NHS ester, NOTA-NCS, DOTA (1,4,7, 10-tetraazacyclododecane-1,4,7,10-tetraacetic acid), DOTA-NHS ester, DOTA-NCS, DOTA-Bz-NCS, tris(t-bu) DOTA, HBED-CC-TFP ester, DTPA (diethylenetriamine-penta-acetic acid), DO3A (1,4,7,10-tetraazacyclododecane-1,4,7-triacetic acid), NODAGA (1,4,7-triazacyclononane, 1-glutaric acid-4,7-acetic acid), TETA (1,4,8,11-tetraazacyclotetradecane-N,N',N'',N'''-tetraacetic acid), TE3A (1,4,8, 11-tetraazacyclotetradecane-1,4,8-triacetic acid), TE2A (1,4, 8,11-tetraazabicyclohexadecane-4,11-diacetic acid), PCTA (3,6,9,15-tetraazabicyclo[9.3.1]pentadeca-1,11,13-triene-3, 6,9,-triacetic acid), cyclen, cyclam) and DFO (deferrioxamine).

The compound or pharmaceutically acceptable salt thereof can be prepared by the following reaction scheme:

(Reaction Scheme 1)

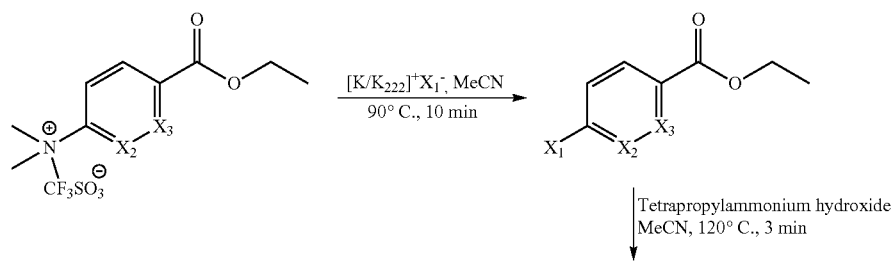

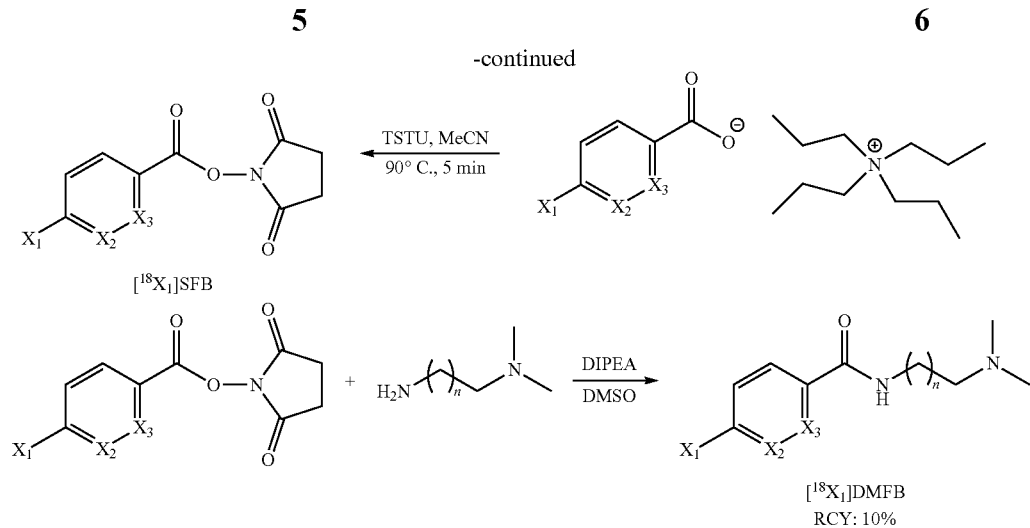

[¹⁸X₁]SFB

[¹⁸X₁]DMFB
RCY: 10%

In addition, the above-mentioned radioactive compound may be synthesized through a substitution reaction with a radioactive salt such as K¹⁸F, K⁷⁶Br or K¹²³I(See Examples 3-2 to 3-5) after synthesizing the compound as a non-radioactive compound comprising a non-radioactive halogen element.

The radioactive compound may be selected from the group consisting of:

N-(2-(dimethylamino)ethyl)-4-[¹⁸F]fluorobenzamide, N-(2-(dimethylamino)ethyl)-4-[¹²³I]iodobenzamide, N-(2-(dimethylamino)ethyl)-4-[¹²⁴I]iodobenzamide, N-(2-(dimethylamino)ethyl)-4-[¹³¹I]iodobenzamide, N-(2-(dimethylamino)ethyl)-4-[⁷⁶Br]bromobenzamide, N-(3-(dimethylamino)propyl)-4-[¹⁸F]fluorobenzamide, N-(3-(dimethylamino)propyl)-4-[¹²³I]iodobenzamide, N-(3-(dimethylamino)propyl)-4-[¹²⁴I]iodobenzamide, N-(3-(dimethylamino)propyl)-4-[¹³¹I]iodobenzamide, N-(3-(dimethylamino)propyl)-4-[⁷⁶Br]bromobenzamide, N-(4-(dimethylamino)butyl)-4-[¹⁸F]fluorobenzamide, N-(4-(dimethylamino)butyl)-4-[¹²³I]iodobenzamide, N-(4-(dimethylamino)butyl)-4-[¹²⁴I]iodobenzamide, N-(4-(dimethylamino)butyl)-4-[¹³¹I]iodobenzamide, N-(4-(dimethylamino)butyl)-4-[⁷⁶Br]bromobenzamide, N-(5-(dimethylamino)pentyl)-4-[¹⁸F]fluorobenzamide, N-(5-(dimethylamino)pentyl)-4-[¹²³I]iodobenzamide, N-(5-(dimethylamino)pentyl)-4-[¹²⁴I]iodobenzamide, N-(5-(dimethylamino)pentyl)-4-[¹³¹I]iodobenzamide, N-(5-(dimethylamino)pentyl)-4-[⁷⁶Br]bromobenzamide, N-(6-(dimethylamino)hexyl)-4-[¹⁸F]fluorobenzamide, N-(6-(dimethylamino)hexyl)-4-[¹²³I]iodobenzamide, N-(6-(dimethylamino)hexyl)-4-[¹²⁴I]iodobenzamide, N-(6-(dimethylamino)hexyl)-4-[¹³¹I]iodobenzamide, N-(6-(dimethylamino)hexyl)-4-[⁷⁶Br]bromobenzamide, N-(2-(dimethylamino)ethyl)-6-[¹⁸F]fluoronicotimamide, N-(2-(dimethylamino)ethyl)-6-[¹²³I]iodonicotimamide, N-(2-(dimethylamino)ethyl)-6-[¹²⁴I]iodonicotinamide, N-(2-(dimethylamino)ethyl)-6-[¹³¹I]iodonicotinamide, N-(2-(dimethylamino)ethyl)-6-[⁷⁶Br]bromonicotinamide, N-(3-(dimethylamino)propyl)-6-[¹⁸F]fluoronicotinamide, N-(3-(dimethyl amino)propyl)-6-[¹²³I]iodonicotinamide, N-(3-(dimethylamino)propyl)-6-[¹²⁴I]iodonicotinamide, N-(3-(dimethylamino)propyl)-6-[¹³¹I]iodonicotinamide, N-(3-(dimethylamino)propyl)-6-[⁷⁶Br]bromonicotinamide, N-(4-(dimethyl amino)butyl)-6-[¹⁸F]fluoronicotinamide, N-(4-(dimethylamino)butyl)-6-[¹²³I]iodonicotinamide, N-(4-(dimethylamino)butyl)-6-[¹²⁴I]iodonicotinamide, N-(4-(dimethylamino)butyl)-6-[¹³¹I]iodonicotinamide, N-(4-(dimethylamino)butyl)-6-[⁷⁶Br]bromonicotinamide, N-(5-(dimethylamino)pentyl)-6-[¹⁸F]fluoronicotinamide, N-(5-(dimethylamino)pentyl)-6-[¹²³I]iodonicotinamide, N-(5-(dimethylamino)pentyl)-6-[¹²⁴I]iodonicotinamide, N-(5-(dimethyl amino)pentyl)-6-[¹³¹I]iodonicotinamide, N-(5-(dimethylamino)pentyl)-6-[⁷⁶Br]bromonicotinamide, N-(6-(dimethyl amino)hexyl)-6-[¹⁸F]fluoronicotinamide, N-(6-(dimethylamino)hexyl)-6-[¹²³I]iodonicotinamide, N-(6-(dimethylamino)hexyl)-6-[¹²⁴I]iodonicotinamide, N-(6-(dimethyl amino)hexyl)-6-[¹³¹I]iodonicotinamide, N-(6-(dimethylamino)hexyl)-6-[⁷⁶Br]bromonicotinamide, N-(2-(dimethylamino)ethyl)-5-[¹⁸F]fluoropicolinamide, N-(2-(dimethyl amino)ethyl)-5-[¹²³I]iodopicolinamide, N-(2-(dimethyl amino)ethyl)-5-[¹²⁴I]iodopicolinamide, N-(2-(dimethylamino)ethyl)-5-[¹³¹I]iodopicolinamide, N-(2-(dimethylamino)ethyl)-5-[⁷⁶Br]bromopicolinamide, N-(3-(dimethylamino)propyl)-5-[¹⁸F]fluoropicolinamide, N-(3-(dimethylamino)propyl)-5-[¹²³I]iodopicolinamide, N-(3-(dimethyl amino)propyl)-5-[¹²⁴I]iodopicolinamide, N-(3-(dimethylamino)propyl)-5-[¹³¹I]iodopicolinamide, N-(3-(dimethylamino)propyl)-5-[⁷⁶Br]bromopicolinamide, N-(4-(dimethyl amino)butyl)-5-[¹⁸F]fluoropicolinamide, N-(4-(dimethyl amino)butyl)-5-[¹²³I]iodopicolinamide, N-(4-(dimethylamino)butyl)-5-[¹²⁴I]iodopicolinamide, N-(4-(dimethyl amino)butyl)-5-[¹³¹I]iodopicolinamide, N-(4-(dimethylamino)butyl)-5-[⁷⁶Br]bromopicolinamide, N-(5-(dimethylamino)pentyl)-5-[¹⁸F]fluoropicolinamide, N-(5-(dimethylamino)pentyl)-5-[¹²³I]iodopicolinamide, N-(5-(dimethylamino)pentyl)-5-[¹²⁴I]iodopicolinamide, N-(5-(dimethyl amino)pentyl)-5-[¹³¹I]iodopicolinamide, N-(5-(dimethylamino)pentyl)-5-[⁷⁶Br]bromopicolinamide, N-(6-(dimethyl amino)hexyl)-5-[¹⁸F]fluoropicolinamide, N-(6-(dimethylamino)hexyl)-5-[¹²³I]iodopicolinamide, N-(6-(dimethylamino)hexyl)-5-[¹²⁴I]iodopicolinamide, N-(6-(dimethylamino)hexyl)-5-[¹³¹I]iodopicolinamide, N-(6-(dimethylamino)hexyl)-5-[⁷⁶Br]bromopicolinamide, N-(2-(dimethylamino)ethyl)-6-[¹⁸F]fluoropyridazine-3-carboxamide, N-(2-(dimethylamino)ethyl)-6-[¹²³I]iodopyridazine-3-carboxamide, N-(2-(dimethyl amino)ethyl)-6-[¹²⁴I]iodopyridazine-3-carboxamide, N-(2-(dimethylamino)ethyl)-6-[¹³¹I]iodopyridazine-3-carboxamide, N-(2-(dimethylamino)ethyl)-6-[⁷⁶Br]bromopyridazine-3-carboxamide, N-(3-(dimethylamino)propyl)-6-[¹⁸F]fluoropyridazine-3-carboxamide, N-(3-(dimethylamino)propyl)-6-[¹²³I]iodopyridazine-3- carboxamide, N-(3-(dimethylamino)propyl)-6-[$^{124}$I]iodopyridazine-3-carboxamide, N-(3-(dimethylamino)propyl)-6-[$^{131}$I]iodopyridazine-3-carboxamide, N-(3-(dimethylamino)propyl)-6-[$^{76}$Br]bromopyridazine-3-carboxamide, N-(4-(dimethylamino)butyl)-6-[$^{18}$F]fluoropyridazine-3-carboxamide, N-(4-(dimethylamino)butyl)-6-[$^{123}$I]iodopyridazine-3-carboxamide, N-(4-(dimethylamino)butyl)-6-[$^{124}$I]iodopyridazine-3-carboxamide, N-(4-(dimethylamino)butyl)-6-[$^{131}$I]iodopyridazine-3-carboxamide, N-(4-(dimethylamino)butyl)-6-[$^{76}$Br]bromopyridazine-3-carboxamide, N-(5-(dimethylamino)pentyl)-6-[$^{18}$F]fluoropyridazine-3-carboxamide, N-(5-(dimethylamino)pentyl)-6-[$^{123}$I]iodopyridazine-3-carboxamide, N-(5-(dimethylamino)pentyl)-6-[$^{124}$I]iodopyridazine-3-carboxamide, N-(5-(dimethylamino)pentyl)-6-[$^{131}$I]iodopyridazine-3-carboxamide, N-(5-(dimethylamino)pentyl)-6-[$^{76}$Br]bromopyridazine-3-carboxamide, N-(6-(dimethylamino)hexyl)-6-[$^{18}$F]fluoropyridazine-3-carboxamide, N-(6-(dimethylamino)hexyl)-6-[$^{123}$I]iodopyridazine-3-carboxamide, N-(6-(dimethylamino)hexyl)-6-[$^{124}$I]iodopyridazine-3-carboxamide, N-(6-(dimethylamino)hexyl)-6-[$^{131}$I]iodopyridazine-3-carboxamide, and N-(6-(dimethylamino)hexyl)-6-[$^{76}$Br]bromopyridazine-3-carboxamide.

On the other hand, when $X_1$ is a complex of the chelator and a radioactive metal or salt thereof, it can be prepared by the following reaction scheme 2:

(Reaction Scheme 2)

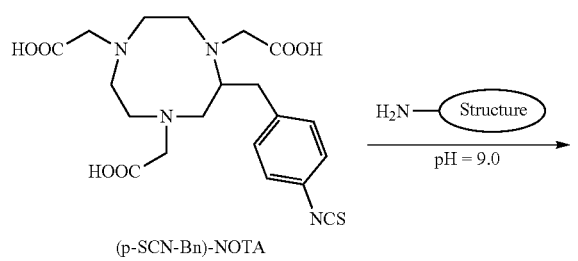
(p-SCN-Bn)-NOTA

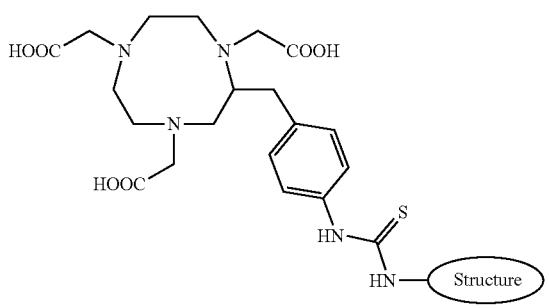

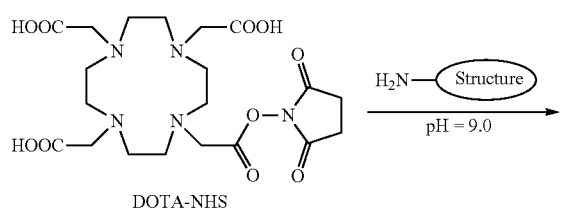
DOTA-NHS

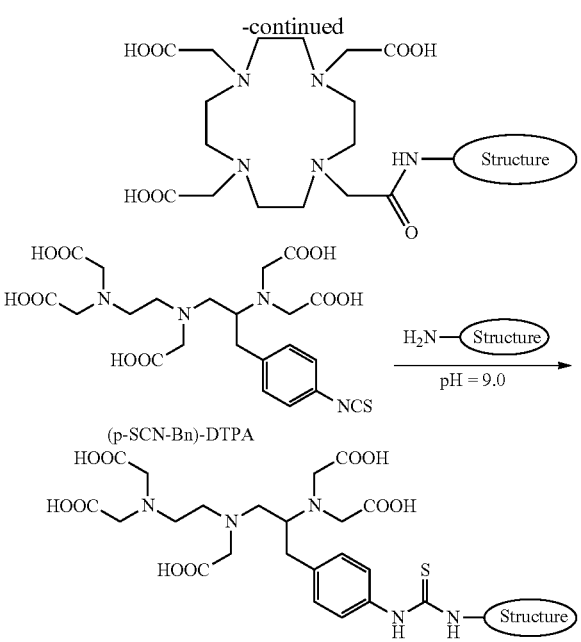
(p-SCN-Bn)-DTPA

The "pharmaceutically acceptable salt" is preferably a salt with an inorganic or organic acid, more preferably a salt having an aliphatic anion such as methoxy, acetoxy, and trifluoroacetoxy anion, a chloride, a bromide, an iodide, aliphatic carboxylate, aromatic or arylaliphatic carboxylate salt, nitrate salts, sulfate salts, phosphate salts, sulfonate salts, mesylate salts, besylate salts and tosylate salts, but not limited thereto. Also the acceptable salt of the present invention include salts with F, Cl$^-$, Br$^-$, or I$^-$. However, the acceptable salts of the present invention are not limited thereto.

In another aspect of the present invention, there is provided a contrast agent for positron emission tomography (PET) imaging comprising the above radioactive compound or an acceptable salt thereof as an active ingredient.

For practical use, the contrast agent for PET imaging according to one embodiment of the present invention may be combined with a pharmaceutically acceptable carrier according to conventional pharmaceutical preparation techniques. Such carriers may have a wide variety of forms depending on the preparation desired, for example, for oral or parenteral administration (including intravenous administration).

In addition, the contrast agent according to one embodiment of the present invention may be administered at a dose of 0.1 mg/kg to 1 g/kg, more preferably 0.1 mg/kg to 500 mg/kg. On the other hand, the dose can be appropriately adjusted according to the age, sex, and condition of the patient within the range of the amount of radiation exposure permitted for the day or the year.

The contrast agent according to one embodiment of the present invention further comprises an inert component, including a pharmaceutically acceptable carrier. As used herein, the term "pharmaceutically acceptable carrier" means any other ingredient than active ingredient in a composition, specially in a pharmaceutical composition. The example of the pharmaceutically acceptable carrier includes binders, disintegrants, diluents, fillers, lubricants, solubilizers or emulsifiers and salts.

The novel contrast agent may be administered to the subject by parenteral administration, and the parenteral administration may be intravenous injection, intraperitoneal injection, intramuscular injection, or subcutaneous injection, but intravenous administration is most preferred.

In another aspect of the present invention, there is provided a method for diagnosing melanoma of a subject comprising administering the above-mentioned radioactive compound to the subject.

The diagnostic method may further include the step of detecting the radiation emitted from the radioactive compound which is accumulated and bound to the melanoma tissue present in the subject after administered from acquired image. The step of detecting the radiation may be performed using a PET imaging device.

BEST MODE FOR CARRYING OUT THE INVENTION

Hereinafter, preferred embodiments of the present disclosure will be described in detail. However, the present disclosure is not limited to embodiments explained herein but may be specified in various aspects. Rather, the embodiments are provided to sufficiently transfer the concept of the present disclosure to a person skilled in the art to thorough and complete contents introduced herein.

Example 1: Preparation of Precursors 1-1: Preparation of Ethyl 4-[Trimethylammonium]Benzoate 0.64 g of ethyl 4-[dimethylamino]benzoate was dissolved in 12 ml of benzene, 0.4 ml of methyl trifluoromethanesulfonate was added, and the mixture was stirred at 85° C. for 6 hours. The reaction was allowed to cool at room temperature and the solvent was removed by distillation under reduced pressure to yield ethyl 4-[trimethylammonium] benzoate as a white product.

The results of 1 H-NMR analysis of the product are shown below:
$^1$H-NMR (300 MHz, CDCl$_3$): 1.34 (t, 3H), 3.64 (s, 9H), 4.36 (q, 2H), 8.12-8.17 (m, 4H).

1-2: Preparation of 5-Bromo-N-(2-(Dimethylamino)Ethyl)Picolinamide 0.5 g of 5-bromopyridine-2-carboxylic acid (0.5 g) dissolved in N,N-dimethylformamide (DMF) and 1.118 g of N,N,N',N'-tetramethyl-O—(N-succinimidyl)uronium tetrafluoroborate (hereinafter abbreviated as 'TSTU') are mixed and N-ethyl-N-isopropylpropan-2-amine (0.647 ml) was added thereto, followed by stirring at 50° C. for 3 hours. Then, 0.244 ml of N, N-dimethylethane-1,2-diamine was added thereto, followed by stirring at room temperature for 2 hours. After 2 hours of the reaction, the reactant was extracted using 50 mL of CH$_2$Cl$_2$ and 100 mL of D.W. from CH$_2$Cl$_2$ layer and filtered after removing residual water from the CH$_2$Cl$_2$ layer using MgSO$_4$. The filtrate was evaporated and the product 5-bromo-N-(2-(dimethylamino)ethyl)picolinamide was purified by column chromatography.

$^1$H-NMR (300 MHz, CD$_3$OD): 2.34 (s, 6H), 2.62 (t, 2H), 3.57 (t, 2H), 7.99-8.01 (m, 1H), 8.13-8.15 (m, 1H), 8.70 (s, 1H).

1-3: Preparation of 6-Bromo-N-(2-(Dimethylamino)Ethyl)Nicotinamide 0.65 g of 6-bromopyridine-3-carboxylic acid dissolved in DMF and 1.453 g of TSTU were mixed, and 0.841 mL of N-ethyl-N-isopropylpropane-2-amine was added, followed by stirring at 50° C. for 3 hours. And then, after adding 0.317 ml of N,N-dimethylethane-1,2-diamine, the mixture was stirred for 2 hours at room temperature. After 2 hours of reaction, the reactant was extracted using 50 mL of CH$_2$Cl$_2$ and 100 mL of D.W. from CH$_2$Cl$_2$ layer and filtered after removing residual water from the CH$_2$Cl$_2$ layer using MgSO$_4$. The filtrate was evaporated and the product, 6-bromo-N-(2-(dimethylamino)ethyl)nicotinamide was purified by column chromatography.

The results of 1 H-NMR analysis of the product are shown below:
$^1$H-NMR (300 MHz, CDCl$_3$): 2.27 (s, 6H), 2.53 (t, 2H), 3.50 (t, 2H), 7.05 (br, 1H), 7.54-7.56 (m, 1H), 7.95-7.98 (m, 1H), 8.73-8.74 (m, 1H).

1-4: Preparation of 5-Bromo-N-(3-(Dimethylamino)Propyl) Picolinamide 0.57 g of 5-bromopyridine-2-carboxylic acid dissolved in DMF and 1.275 g of TSTU were mixed and 0.738 ml of N-ethyl-N-isopropylpropane-2-amine was added, followed by stirring at 50° C. for 3 hours. Then, 0.318 ml of N,N-dimethylpropane-1,3-diamine was added, followed by stirring at room temperature for 2 hours. After 2 hours of reaction, the reactant was extracted using 50 mL of CH$_2$Cl$_2$ and 100 mL of D.W. from CH$_2$Cl$_2$ layer and filtered after removing residual water from the CH$_2$Cl$_2$ layer using MgSO$_4$. The filtrate was evaporated and the product, 5-bromo-N-(3-(dimethylamino)propyl)picolinamide was purified by column chromatography.

The results of $^1$H-NMR analysis of the product are shown below:
$^1$H-NMR (300 MHz, CD$_3$OD): 1.78-1.84 (m, 2H), 2.25 (s, 6H), 2.39-2.42 (m, 2H), 3.44 (t, 2H), 7.98-8.00 (m, 1H), 8.11-8.13 (m, 1H), 8.67-8.68 (m, 1H).

1-5: Preparation of 5-Bromo-N-(4-(Dimethylamino)Butyl)Picolinamide 0.6 g of 5-bromopyridine-2-carboxylic acid dissolved in DMF and 1.342 g of TSTU were added and 0.776 ml of N-ethyl-N-isopropylpropane-2-amine was added thereto, followed by stirring at 50° C. for 3 hours. Then, 0.376 ml of N,N-dimethylbutane-1,4-diamine was added, followed by stirring at room temperature for 2 hours. After 2 hours of reaction, the reactant was extracted using 50 mL of CH$_2$Cl$_2$ and 100 mL of D.W. from CH$_2$Cl$_2$ layer and filtered after removing residual water from the CH$_2$Cl$_2$ layer using MgSO$_4$. The filtrate was evaporated and the product, 5-bromo-N-(4-(dimethylamino)butyl)picolinamide was purified by column chromatography.

The results of $^1$H-NMR analysis of the product are shown below:
$^1$H-NMR (300 MHz, CD$_3$OD): 1.57-1.68 (m, 4H), 2.34 (s, 6H), 2.48-2.51 (m, 2H), 3.43 (t, 2H), 7.99-8.00 (m, 1H), 8.13-8.15 (m, 1H), 8.70-8.71 (m, 1H).

Example 2: Preparation of Standard Compounds 2-1: Synthesis of N-(2-(Dimethylamino)Ethyl)-4-Fluorobenzamide (DMFB)

0.2 g of 4-fluorobenzoic acid dissolved in DMF and 0.645 g of TSTU were added and 0.373 ml of N-ethyl-N-isopropylpropane-2-amine was added thereto, followed by stirring at 50° C. for 3 hours. Then, 0.156 ml of N, N-dimethylethane-1,2-diamine was added, followed by stirring at room temperature for 2 hours. After 2 hours of reaction, the reactant was extracted using 50 mL of $CH_2Cl_2$ and 100 mL of D.W. from $CH_2Cl_2$ layer and filtered after removing residual water from the $CH_2Cl_2$ layer using $MgSO_4$. The filtrate was evaporated and the product, N-(2-(dimethylamino) ethyl)-4-fluorobenzamide was purified by column chromatography and designated as "DMFB".

The results of $^1$H-NMR analysis of the product are shown below:

$^1$H-NMR (300 MHz, $CDCl_3$): 2.23 (s, 6H), 2.48 (t, 2H), 3.47 (q, 2H), 7.0-7.06 (m, 3H), 7.77-7.81 (m, 2H)

The present inventors designated the compound as "DMFB".

2-2: Preparation of N-(2-(Dimethylamino)Ethyl)-5-Fluoropicolinamide (DMPY2)

0.25 g of 5-fluoropyridine-2-carboxylic acid dissolved in DMF and 0.8 g of TSTU were added and 0.463 ml of N-ethyl-N-isopropylpropane-2-amine was added, followed by stirring at 50° C. for 3 hours. Then, 0.175 ml of N,N-dimethylethane-1,2-diamine was added thereto, followed by stirring at room temperature for 2 hours. After 2 hours of reaction, the reactant was extracted using 50 mL of $CH_2Cl_2$ and 100 mL of D.W. from $CH_2Cl_2$ layer and filtered after removing residual water from the $CH_2Cl_2$ layer using $MgSO_4$. The filtrate was evaporated and the product, N-(2-(dimethylamino) ethyl)-5-fluoropicolinamide was purified by column chromatography and was designated as "DMPY2".

The results of $^1$H-NMR analysis of the product are shown below:

$^1$H-NMR (300 MHz, $CDCl_3$): 2.31 (s, 6H), 2.56 (t, 2H), 3.54 (q, 2H), 7.48-7.52 (m, 1H), 8.15-8.21 (m, 2H), 8.37-8.38 (m, 1H).

2-3: Preparation of N-2-(Dimethylamino)Ethyl)-6-Fluoronicotinamide (DMPY3)

0.28 g of 6-fluoropyridine-3-carboxylic acid dissolved in DMF and 0.897 g of TSTU were mixed, and 0.519 ml of N-ethyl-N-isopropylpropane was added, followed by stirring at 50° C. for 3 hours. Then, 0.195 ml of N,N-dimethylpropane-2-amine was added, followed by stirring at room temperature for 2 hours. After 2 hours of reaction, the reactant was extracted using 50 mL of $CH_2Cl_2$ and 100 mL of D.W. from $CH_2Cl_2$ layer and filtered after removing residual water from the $CH_2Cl_2$ layer using $MgSO_4$. The filtrate was evaporated and the product, N-(2-(dimethylamino)ethyl)-6-fluoronicotinamide was purified by column chromatography and designated as "DMPY3".

The results of $^1$H-NMR analysis of the product are shown below:

$^1$H-NMR (300 MHz, $CDCl_3$): 2.25 (s, 6H), 2.51 (t, 2H), 3.50 (q, 2H), 6.97-7.00 (m, 2H), 8.22-8.26 (m, 1H), 8.62-8.63 (m, 1H).

2-4: Preparation of N-(3-(Dimethylamino)Propyl)-5-Fluoropicolinamide (3DMPY2)

0.26 g of 5-fluoropyridine-2-carboxylic acid dissolved in DMF and 0.833 g of TSTU were mixed and 0.482 ml of N-ethyl-N-isopropylpropane-2-amine was added, followed by stirring at 50° C. for 3 hours. Then, 0.208 ml of N,N-dimethylpropane-1,3-diamine was added thereto, followed by stirring at room temperature for 2 hours. After 2 hours of reaction, the reactant was extracted using 50 mL of $CH_2Cl_2$ and 100 mL of D.W. from $CH_2Cl_2$ layer and filtered after removing residual water from the $CH_2Cl_2$ layer using $MgSO_4$. The filtrate was evaporated and the product, N-(3-(dimethylamino)propyl)-5-fluoropicolinamide was purified by column chromatography and designated as "3DMPY2".

The results of $^1$H-NMR analysis of the product are shown below:

$^1$H-NMR (300 MHz, $CD_3OD$): 1.82-1.88 (m, 2H), 2.34 (s, 6H), 2.50-2.53 (m, 2H), 3.46 (t, 2H), 7.72-7.76 (m, 1H), 8.14-8.17 (m, 1H), 8.51-8.52 (m, 1H).

2-5: Preparation of N-(4-(Dimethylamino) Butyl)-5-Fluoropicolinamide (4DMPY2)

0.3 g of 5-fluoropyridine-2-carboxylic acid dissolved in MF and 0.96 g of TSTU were mixed and 0.556 ml of N-ethyl-N-isopropylpropane-2-amine was added, followed by stirring at 50° C. for 3 hours. Then, 0.27 ml of N,N-dimethylbutane-1,4-diamine was added, followed by stirring at room temperature for 2 hours. After 2 hours of reaction, the reactant was extracted using 50 mL of $CH_2Cl_2$ and 100 mL of D.W. from $CH_2Cl_2$ layer and filtered after removing residual water from the $CH_2Cl_2$ layer using $MgSO_4$. The filtrate was evaporated and the product, N-(4-(dimethylamino) butyl)-5-fluoropicolinamide was purified by column chromatography and designated as "4DMPY2".

The results of $^1$H-NMR analysis of the product are shown below:

$^1$H-NMR (300 MHz, $CD_3OD$): 1.65-1.75 (m, 4H), 2.674 (s, 6H), 2.90-2.93 (m, 2H), 3.45-3.47 (t, 2H), 7.72-7.76 (m, 1H), 8.14-8.17 (m, 1H), 8.51-8.52 (m, 1H)

Example 3: Preparation of Radioactive Compounds

3-1: Preparation of N-(2-(Dimethylamino)Ethyl)-4-[$^{18}$F]Fluorobenzamide ([$^{18}$F]DMFB)

10 mg of the precursor, ethyl 4-[trimethylammonium] benzoate prepared in Example 1-1 was reacted with a carrier-free $K^{18}F$ in acetonitrile solvent to obtain ethyl 4-[$^{18}$F]fluorobenzoate salt and N-succinimidyl 4-[$^{18}$F]fluorobenzoate was synthesized by adding tetrapropylammonium hydroxide and TSTU. Thereafter, 0.1 ml of N,N-dimethylethyne-1,2-diamine was added to the labeled compound, and the mixture was heated after adding 0.1 mL of N,N-dimethylethane-1,2-diamine and a radioactive compound, N-(2-(dimethylamino)ethyl)-4-[$^{18}$F]fluorobenzamide was synthesized. The synthesized compound was purified using a semi-preparative column and was designated as [$^{18}$F]DMFB.

3-2: Preparation of N-(2-(Dimethylamino)Ethyl)-5-[$^{18}$F] Fluoropicolinamide ([$^{18}$F]DMPY2)

2 mg of 5-bromo-N-(2-dimethylamino)ethyl)picolinamide prepared in Example 1-2 was reacted with a carrier-free $K^{18}F$ in acetonitrile solvent to obtain N-(2-dimethylamino)ethyl)-5-[$^{18}$F]fluoropicolinamide. The synthesized N-(2-dimethylamino)ethyl)-5-[$^{18}$F]fluoropicolinamide was purified using a semi-preparative column and designated as "[$^{18}$F]DMPY2".

3-3: Preparation of N-(2-(Dimethylamino)Ethyl)-6-[$^{18}$F] Fluoronicotinamide ([$^{18}$F]DMPY3)

2 mg of 5-bromo-N-(2-dimethylamino)ethyl)picolinamide prepared in Example 1-3 was reacted with a carrier-free K$^{18}$F in an acetonitrile solvent to obtain N-(2-(dimethylamino)ethyl)-6-[$^{18}$F]fluoropicolinamide. The synthesized N-(2-(dimethylamino)ethyl)-6-[$^{18}$F]fluoropicolinamide was purified using a semi-preparative column and was designated as "[$^{18}$F]DMPY3".

3-4: Preparation of N-(3-(Dimethylamino)Propyl)-5-[$^{18}$F] Fluoropicolinamide ([$^{18}$F]3DMPY2)

2 mg of 5-bromo-N-(3-(dimethylamino)propyl)picolinamide prepared in Example 1-4 was reacted with a carrier-free K$^{18}$F in an acetonitrile solvent to obtain N-(3-(dimethylamino)propyl)-5-[$^{18}$F]fluoropicolinamide. The synthesized N-(3-(dimethylamino)propyl)-5-[$^{18}$F]fluoropicolinamide was purified using a semi-preparative column and was designated as [$^{18}$F]3DMPY2).

3-5: Preparation of N-(4-(Dimethylamino)Butyl)-5-[$^{18}$F] Fluoropicolinamide ([$^{18}$F]4DMPY2)

2 mg of 5-bromo-N-(4-(dimethylamino)butyl)picolinamide prepared in Example 1-5 was reacted with a carrier-free K$^{18}$F in an acetonitrile solvent to obtain N-(4-(dimethylamino)butyl)-5-[$^{18}$F]fluoropicolinamide. The synthesized N-(4-(dimethylamino)butyl)-5-[$^{18}$F]fluoropicolinamide was purified using a semi-preparative column and was designated as "[$^{18}$F]4DMPY2".

Experimental Example 1: In Vitro Stability Test

For in vitro stability test, 0.74 MBq/100 µl of [$^{18}$F] DMFB was dissolved in 1.0 ml human serum and then evaluated at 37° C. for 2 hours. The structural stability was measured by ITLC-sg. ITLC-sg (1×10 cm) was developed using MC:MeOH=10:1. The results were confirmed by radio TLC. As a result, as shown in FIG. 1, [$^{18}$F] DMFB according to an embodiment of the present invention was confirmed to be very stable even after 2 hours.

Experimental Example 2: Melanin Binding Assay 0.74 MBq of [$^{18}$F] DMFB was reacted with 2 mg of melanin and 10 ml of distilled water for 10, 30, 60, and 120 minutes at 37° C. with stirring. Then, centrifugation was performed at 16,800 rpm for 10 minutes, and 100 1 of the supernatant was measured with a gamma counter. Percentages (%) of [$^{18}$F]DMFB bound to melanin were calculated based on the mixture of [$^{18}$F]DMFB and distilled water alone without melanin.

Figure 2:
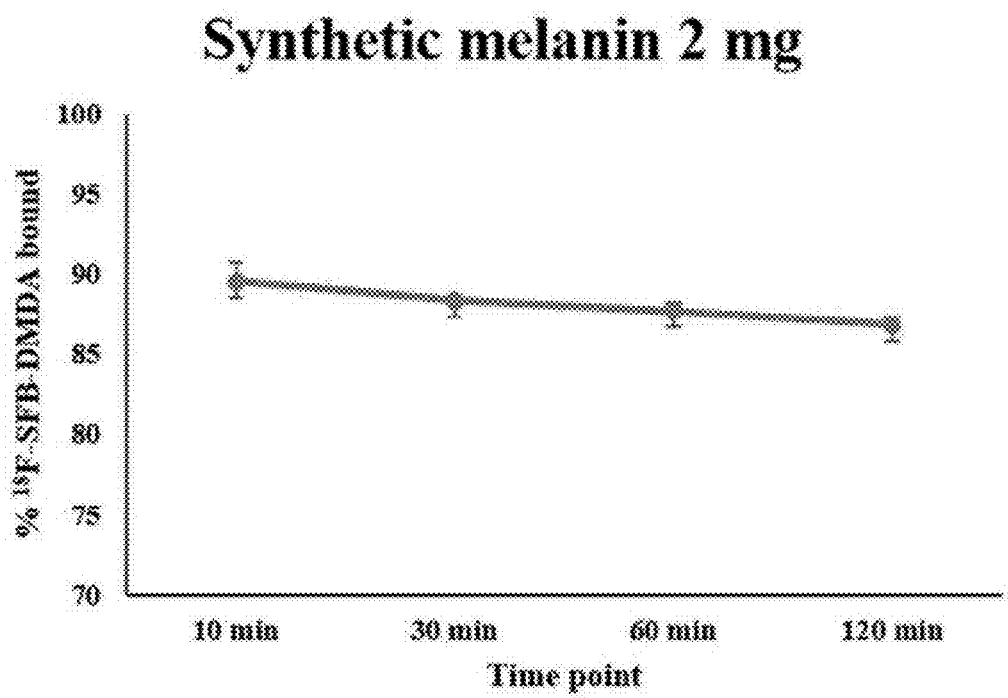
FIG. 2 is a graph showing changes in binding ability over time of [$^{18}$F]DMFB to melanin in vitro according to an embodiment of the present invention.

As a result, as shown in FIG. 2, it was found that the binding rate of [$^{18}$F]DMFB of the present invention was 85% or more and did not significantly decrease even after 120 minutes.

Experimental Example 3: Melanoma Cell Uptake Ratio Experiment

B16F10 cell line, a mouse malignant melanoma cell line, was cultured in 5% $CO_2$ in DMEM medium. Twenty-four hours prior to the experiment, cells were plated at 5×10$^5$ cells/well in 12-well plates and treated with 0.275 mM L-tyrosine-supplemented medium and non-supplemented medium, respectively. Then the cells were treated with 0.74 MBq of [18F]DMFB and incubated at 37° C. for 10, 30, and 60 min, respectively. After washing with PBS twice, the cells were treated with trypsin and the degree of [$^{18}$F]DMFB in the cell culture medium and cells in each time group was measured with a gamma counter, respectively. Three experiments were performed for each time group, and the results were expressed as percentage of the amount absorbed by cells versus the amount treated into the plate.

Figure 3:
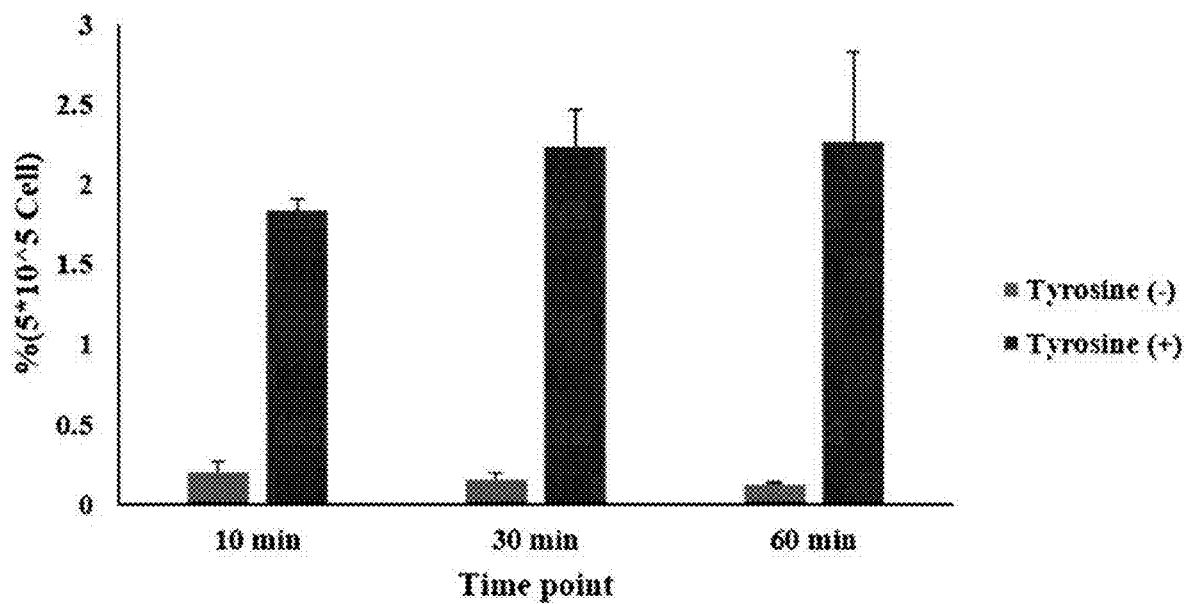
FIG. 3 is a graph showing the extent of in vitro uptake of [$^{18}$F]DMFB by B16F10 melanoma cell line, with or without tyrosine, according to an embodiment of the present invention.

As shown in FIG. 3, the [$^{18}$F]DMFB uptake in the B16F10 melanoma cells in the medium supplemented with tyrosine was significantly increased immediately after 10 minutes, and it did not decrease and increased gradually until the time was increased up to 60 minutes. On the other hand, when L-tyrosine was not treated, it was hardly absorbed.

Experimental Example 4: Examination of the Body Distribution in a Small Animal Model of Tumor Transplantation In order to confirm the in vivo distribution of [$^{18}$F]DMFB, experiments were performed on nude mice whose tumor was grown to 100 to 150 mm$^3$ after about 10 days of injection of the B16F10 cell line into the right shoulder region. [$^{18}$F] DMFB was injected into the tail vein of the tumor-bearing mice at a dose of 7.4 MBq and sacrificed at 10, 30, 60, and 120 minutes, respectively to excise tumor tissue, blood and organs, and distribution of the radioactive compound was confirmed. The excised organs were measured by the gamma counter in each of the organs including blood, heart, lung, liver, spleen, stomach, intestine, kidney, pancreas, normal muscle, bone, brain, skin and eyes. The results were corrected by organ weight and expressed as a percentage of injections per gram of tissue (% ID/g).

In addition, in order to confirm the in vivo distribution of [$^{18}$F]DMPY2 prepared in the example 3-2, experiments were performed on nude mice whose tumors were grown to 100 to 150 mm$^3$ after about 10 days of injection of the B16F10 cell line into the right shoulder region. [$^{18}$F] DMPY2 was injected into the tail vein of the tumor-bearing mice at a dose of 7.4 MBq and sacrificed at 10, 30, and 60 minutes, respectively to excise tumor tissue, blood and organs, and distribution of the radioactive compound was confirmed. The excised organs were measured by the gamma counter in each of the organs including blood, heart, lung, liver, spleen, stomach, intestine, kidney, pancreas, normal muscle, bone, brain, skin and eyes. The results were corrected by organ weight and expressed as a percentage of injections per gram of tissue (% ID/g).

Figure 4A:
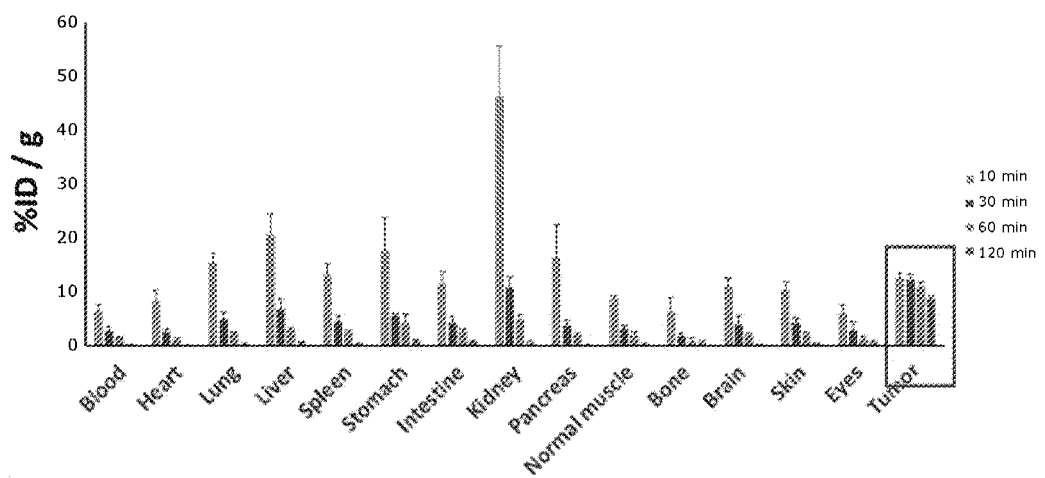
FIG. 4A is a graph showing the absorption ratio (ID/g) over time (10 min, 30 min, 60 min and 120 min) from the injection of [$^{18}$F]DMFB into a melanoma model mouse according to an embodiment of the present invention.
Figure 4B:
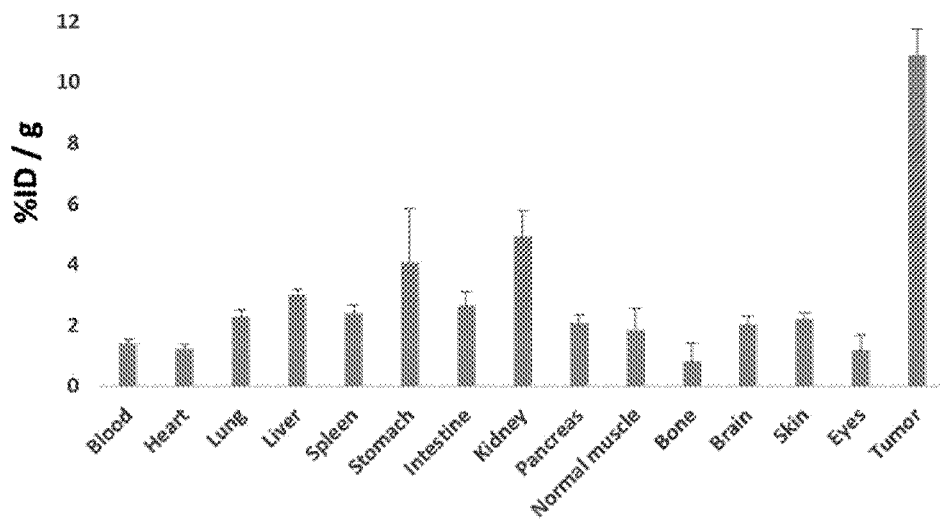
FIG. 4B is a graph showing the absorption ratio in each organ or cancer lesion at the elapse of 60 minutes.
Figure 4C:
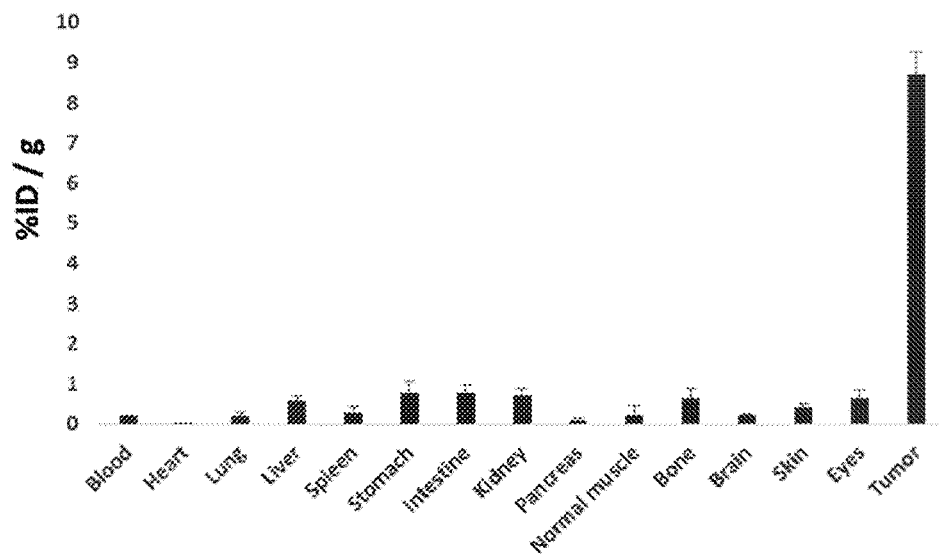
FIG. 4C is a graph showing the absorption ratio in each organ and cancer lesion at 120 minutes from the injection of [$^{18}$F]DMFB.
Figure 4D:
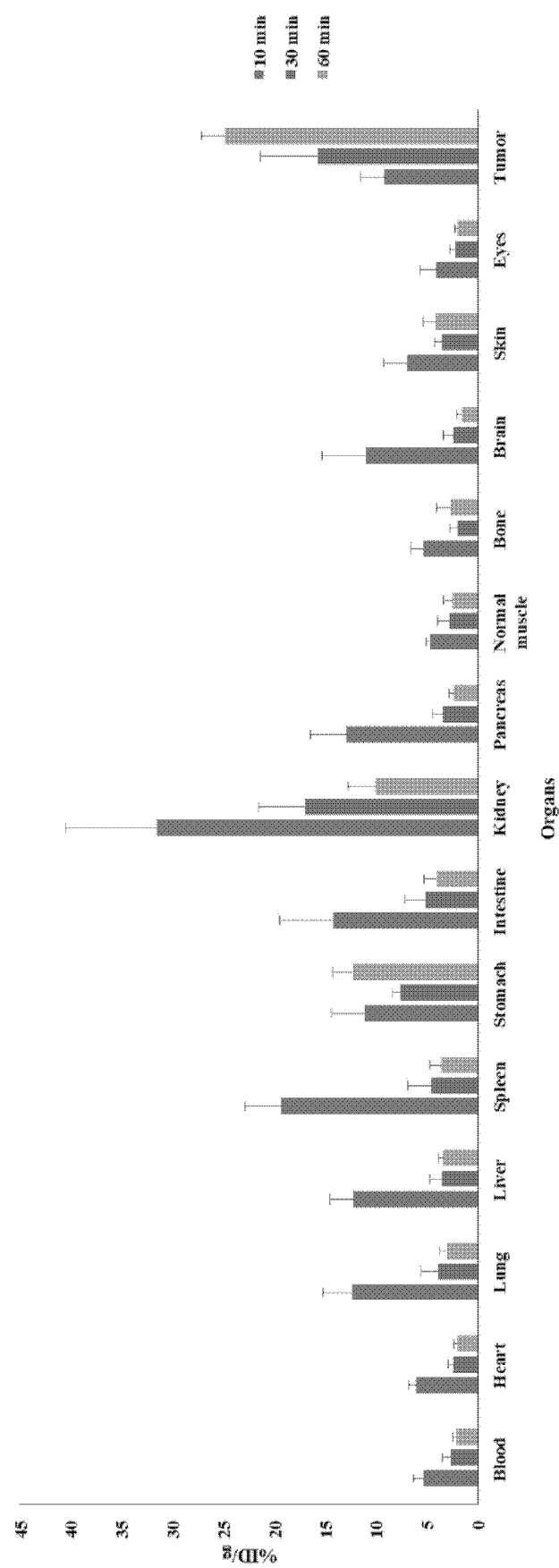
FIG. 4D is a graph showing the absorption ratio (ID/g) over time (10 min, 30 min, and 60 min) from the injection of [$^{18}$F]DMPY2 into a melanoma model mouse according to an embodiment of the present invention

As a result, as shown in FIGS. 4A to 3C, strong radioactivity was detected in many internal organs such as blood, heart, liver, lung, and kidney after 10 minutes of injection of [$^{18}$F]DMFB. However, it was found that the radioactivity in the tumor tissue was maintained while the radioactivity in the visceral organs was hardly detected at the elapsed time of 2 hours (FIG. 4C). In particular, as shown in FIG. 4B, the absorption ratio in tumor tissues was the highest at 1 hour after injection of [$^{18}$F]DMFB which is same as the imaging time of conventional PET, whereas the absorption ratio in stomach, liver, and kidney was relatively low. In addition, as shown in FIG. 4D, [$^{18}$F]DMPY2 also was accumulated most in tumor tissue at 1 hour after injection, and the signal is rapidly decreased in other organs such as kidney.

Therefore, it can be seen that the radioactive compound according to one embodiment of the present invention can be very usefully used for identification of a lesion. The tumor tissue-specific imaging ability of the radioactive compound according to one embodiment of the present invention compared to other organs was superior to the 18F-FBZA described in the above-mentioned prior arts.

Experimental Example 5: PET Imaging Using Xenograft Tumor Mouse Model

To confirm the in vivo dynamics of [$^{18}$F]DMFB, B16F10 cell line was injected into the right shoulder region, and about 10 days later, micro PET was performed using a nude mouse bearing tumor ranging in size of 100-150 mm$^3$. The nude mice were anesthetized with Isoflurane inhalation and then injected with 7.4 MBq of [$^{18}$F]DMFB into the tail vein. Static micro PET images were obtained at 10, 30, and 60 minutes after injection of the radioactive compound. Tumor uptake was determined and the images were reconstructed using 3D-ordered subset expectation maximization (3D-OSEM).

In addition, the in vivo dynamics of [$^{18}$F] DMPY2 was also analyzed by the same method as described above except that micro PET images were taken at 30 and 60 minutes after injection.

Figure 5A:
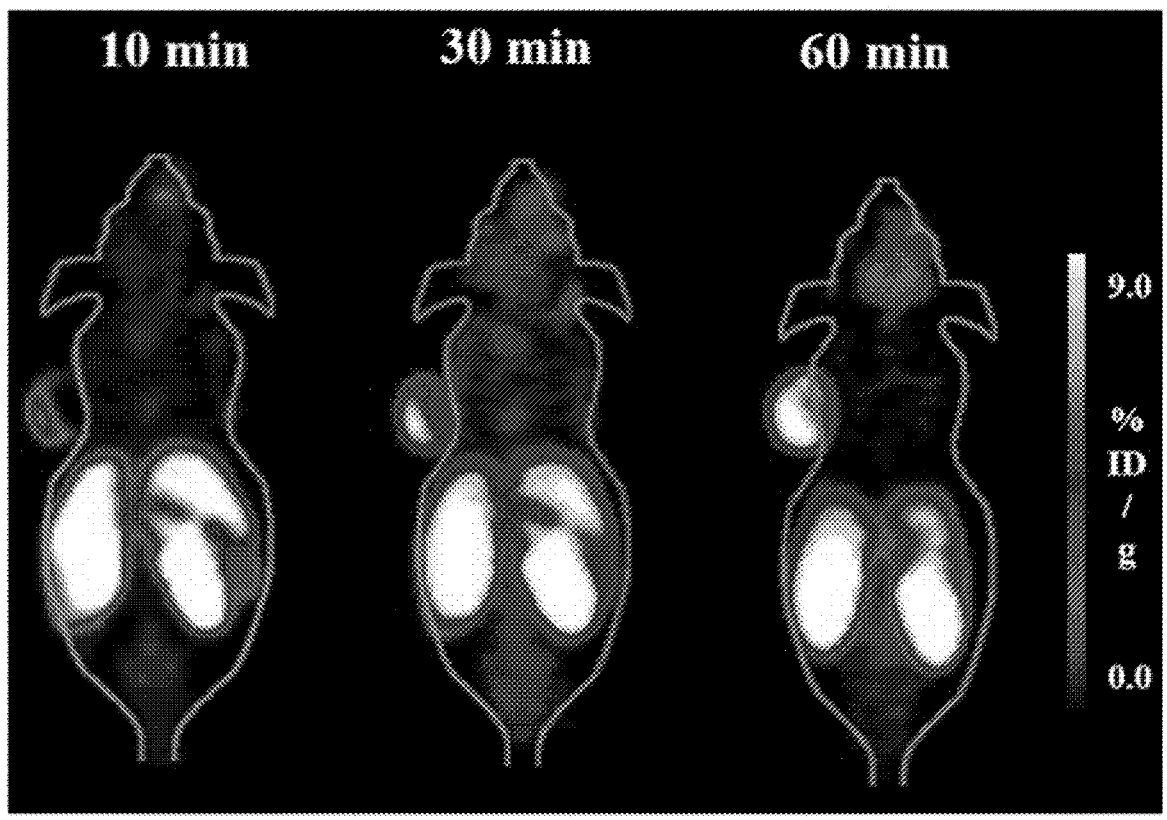
FIG. 5A is a micro PET image taken from tumor model mice according to passage of time (10 min, 30 min and 60 min) after injecting [$^{18}$F]DMFB into melanoma model mice according to one embodiment of the present invention.
Figure 5B:
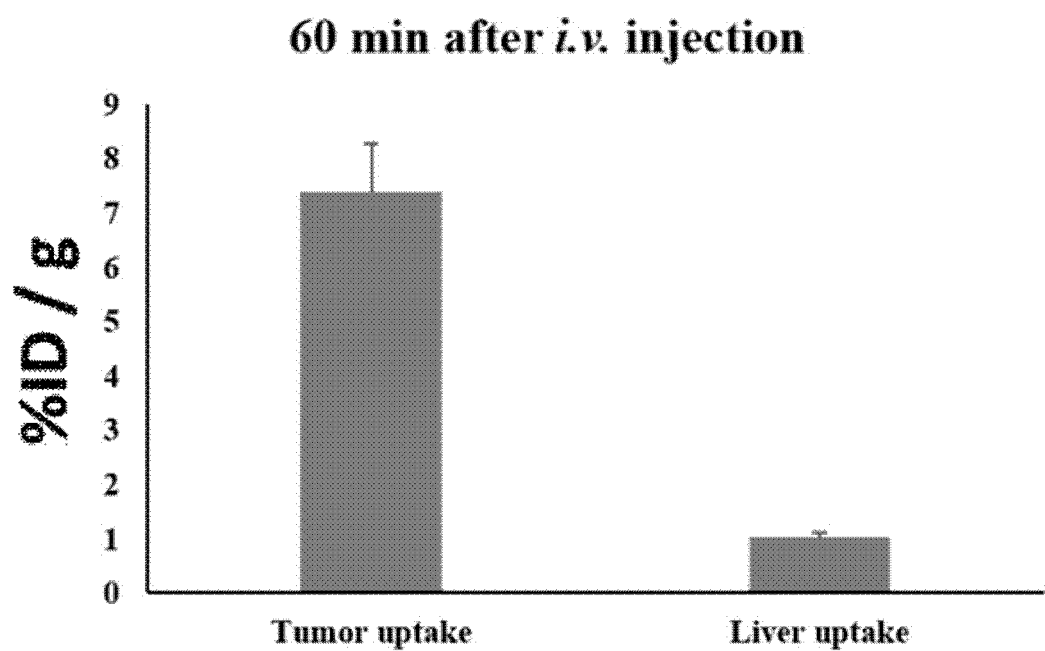
FIG. 5B is a graph representing uptake ration in the tumor tissue and liver after 60 min from the injection of [$^{18}$F]DMFB.
Figure 5C:
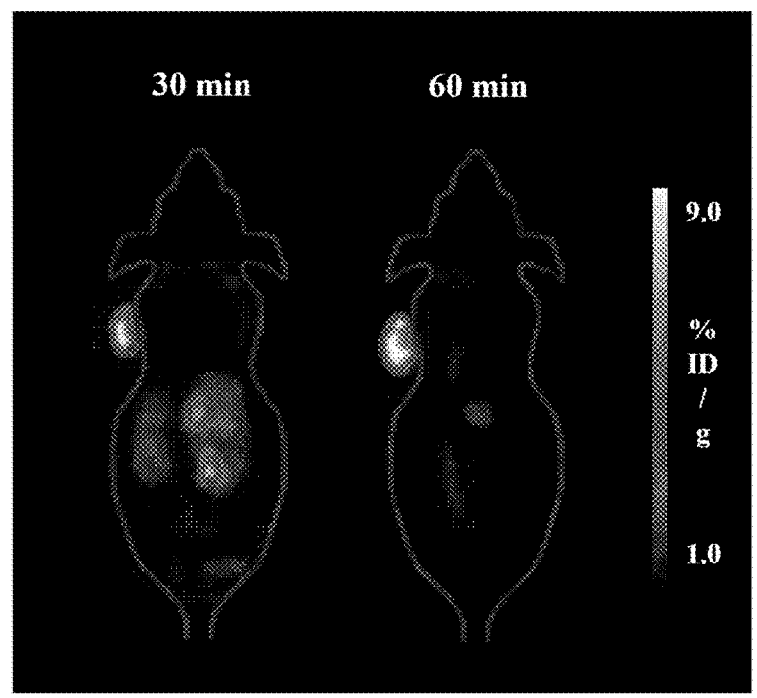
FIG. 5C is a micro PET image taken from tumor model mice according to passage of time (30 min and 60 min) after injecting [$^{18}$F]DMPY2 into melanoma model mice according to one embodiment of the present invention.
Figure 6A:
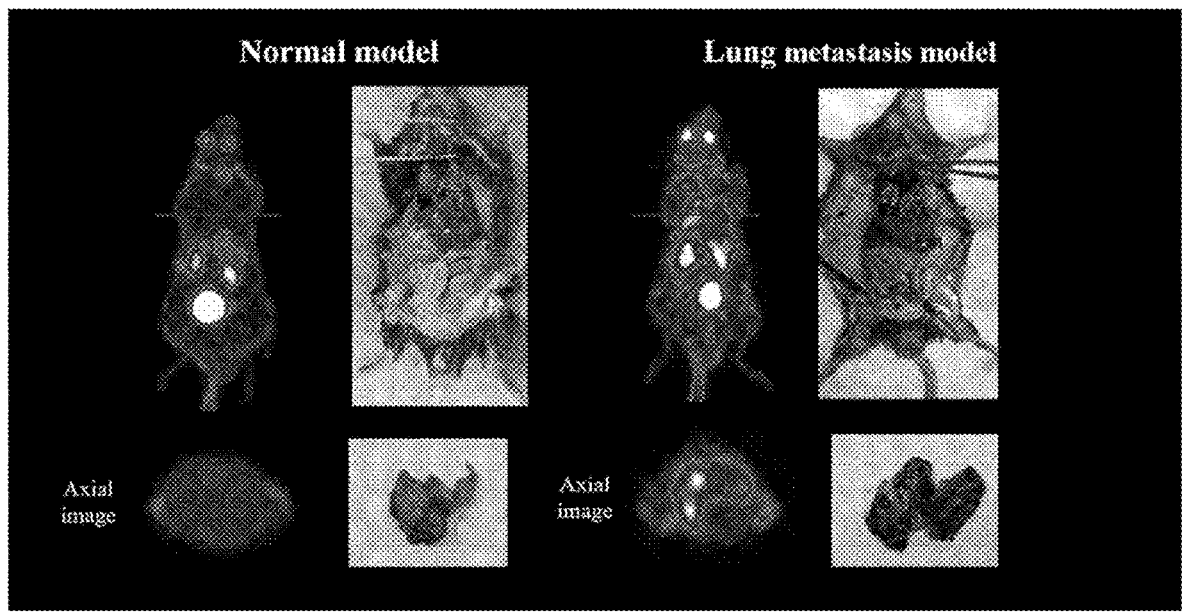
FIG. 6A is a micro PET image showing that it is possible to detect a lung metastatic cancer at 60 minutes from administering [$^{18}$F]DMFB according to an embodiment of the present invention to a normal model (left) and a lung metastasis model animal (right), respectively.
Figure 6B:
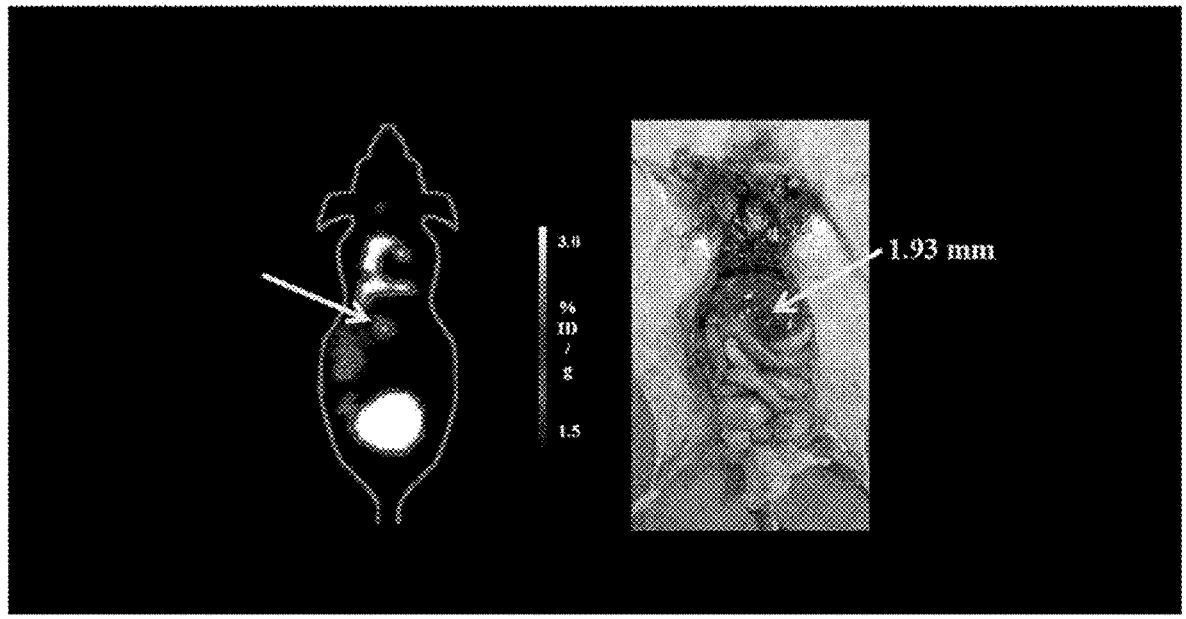
FIG. 6B is a micro PET image (left) and a photograph showing internal organs (right) taken from a liver metastasis model mouse administered with [$^{18}$F]DMFB according to an embodiment of the present invention after 60 min from the injection.
Figure 6C:
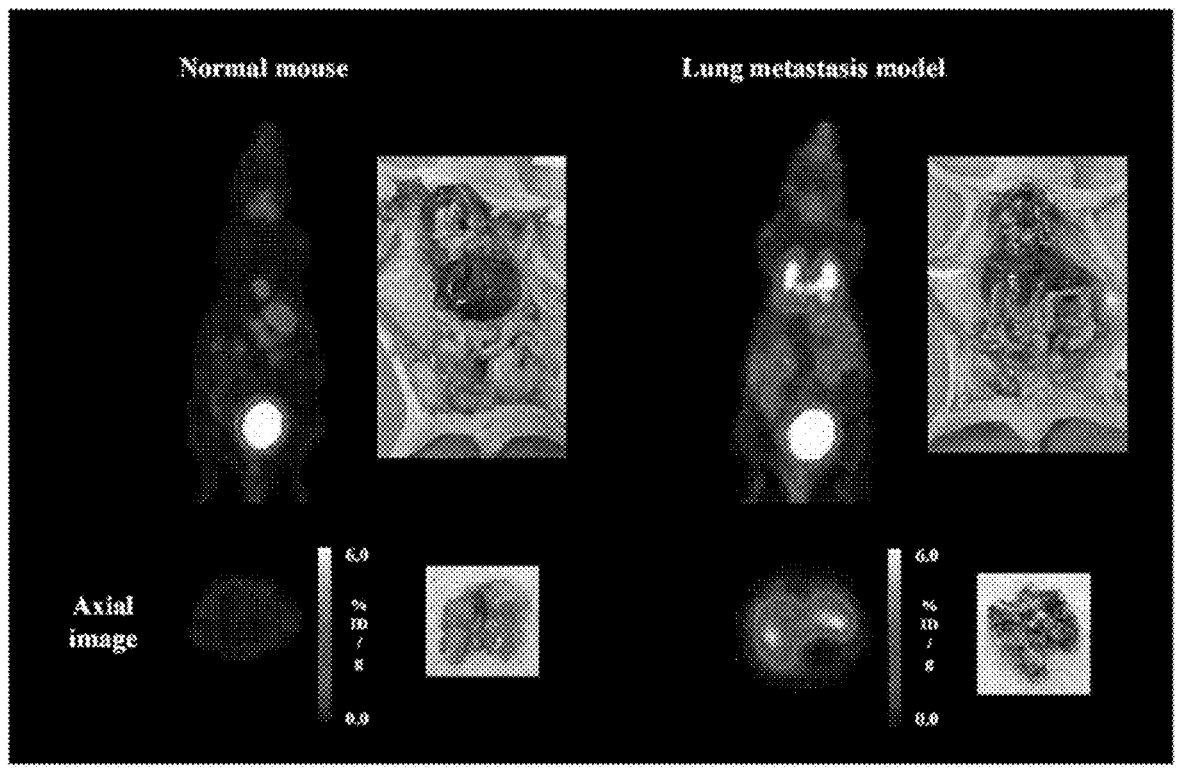
FIG. 6C is a micro PET image taken from a lung metastasis model mouse (right) and a normal mouse (left) administered with [$^{18}$F]DMPY2 according to an embodiment of the present invention after 60 min from the injection, respectively.
Figure 6D:
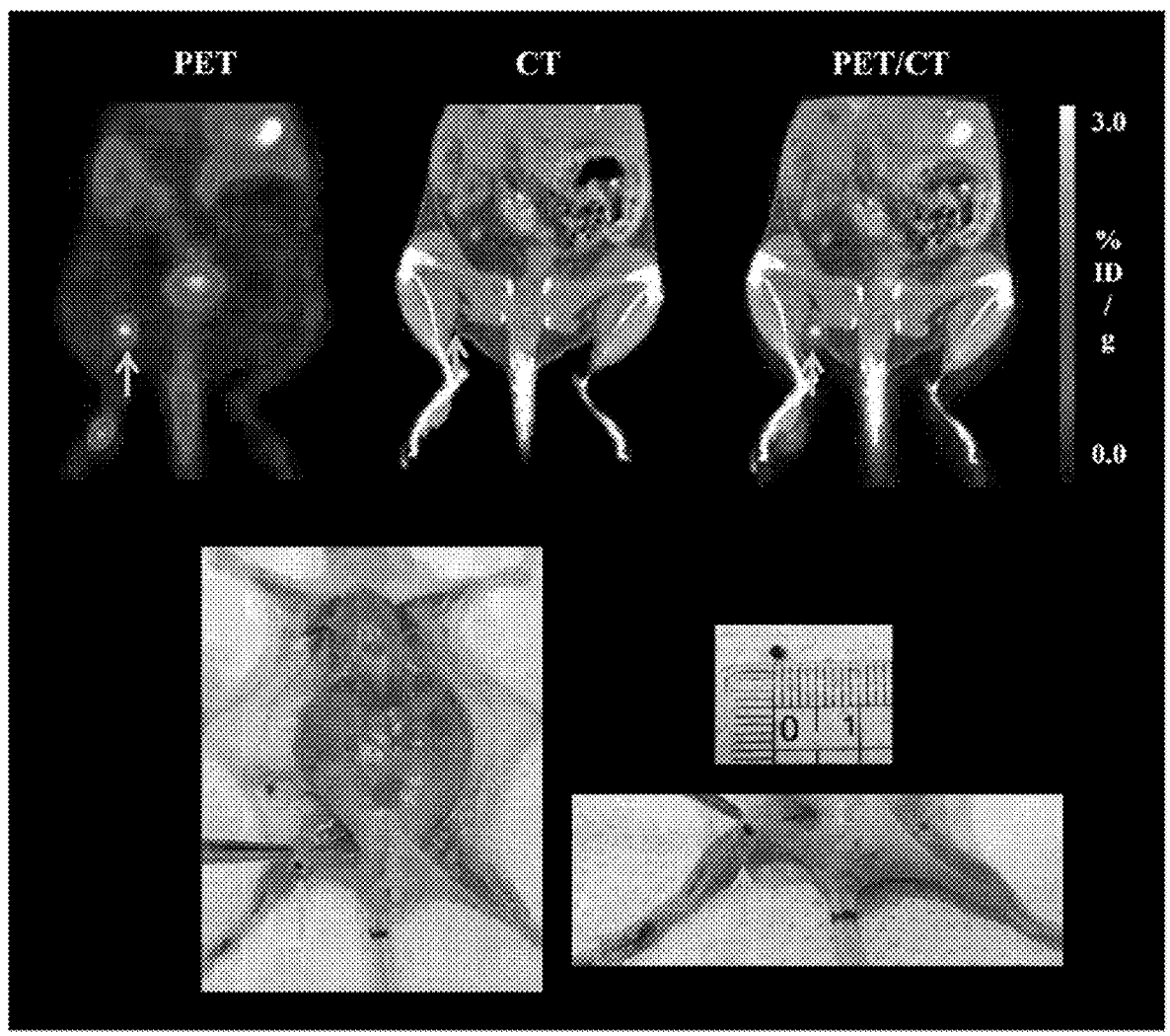
FIG. 6D is a series of images including a micro PET image (upper left), a CT image (upper center), a PET/CT image (upper right) taken from lymph node metastasis model mice administered with [$^{18}$F]DMPY2 according to an embodiment of the present invention after 60 min from the injection, a photograph showing a lymph node (arrows) where the metastasis has occurred in the experimental animals (lower left), an enlarged photograph of the lymph node (lower right), and an enlarged photograph of the excised lymph node.

As a result, as shown in FIGS. 5A and 5B, the radioactivity in the liver decreased with time after the injection of [$^{18}$F]DMFB, while the radiation in the tumor tissue was maintained. In addition, as shown in FIG. 5C, [$^{18}$F]DMPY2 according to one embodiment of the present invention was also clearly observed in melanoma tumor tissue at 1 hour after injection, and signals in other organs were very weak. This is better than the result of [$^{18}$F] DMFB maintaining signal in other organs at 60 min after injection.

Experimental Example 6: In Vivo Distribution and PET Imaging in Lung/Liver Metastatic Model Mice In order to examine the in vivo distribution and dynamics of [$^{18}$F]DMFB in lung/liver metastatic animal model, the present inventors divided C57BL/6 mice into two groups, one were injected with 1×10$^5$ cells of B16F10 cell line into the tail vein and the other were not injected with the tumor cells. After 14 days from the tumor cell inoculation, 7.4 MBq of [$^{18}$F]DMFB was injected into lung metastatic model mice and normal mice via tail vein, respectively and visualized at 60 min. Likewise, liver metastatic mice prepared by injecting 1×10$^5$ cells of B16F10 cell line into the tale vein were injected with 7.4 MBq of [$^{18}$F]DMFB into the tail vein. After 60 minutes of the administration, micro PET image was obtained. This liver metastatic model mice were produced among mice survived after a certain time after the induction of lung metastasis. Mice survived after the induction lung metastasis have metastasized to the lymph nodes and other organs after time elapse. Liver metastatic mice were selected by micro PET images using [$^{18}$F]FDG, and micro PET images using [$^{18}$F]FDG were used as a positive control for [$^{18}$F]DMFB according to one embodiment of the present invention. Static images were reconstructed using 3D-ordered subset expectation maximization (3D-OSEM). After obtaining the images, the metastatic model mice and normal mice were sacrificed and lung and liver were excised and uptake ratio of the excised lung and liver were measured by a gamma counter. The results were corrected by organ weight and expressed as a percentage of injections per gram of tissue (% ID/g).

In addition, the present inventors performed the in vivo distribution and dynamics of [$^{18}$F]DMPY2 in spontaneous lung/liver/lymph node metastatic animal models. Particularly, the present inventors prepared lung, lymph node and liver metastasis model mice, respectively, as described above. Metastatic mice were selected by micro PET images using [$^{18}$F]FDG, and micro PET images using [$^{18}$F]FDG were used as a positive control for [$^{18}$F]DMPY2 according to one embodiment of the present invention. Static images were reconstructed using 3D-ordered subset expectation maximization (3D-OSEM).

As a result of the above analysis, as shown in FIGS. 6A to 6E, the metastatic foci were successfully imaged.

Therefore, the radioactive compound according to one embodiment of the present invention can be very usefully used for the diagnosis of melanoma and even for the detection of metastasis thereof.

Experimental Example 7: Comparison Between [$^{18}$F]DMPY2 and [$^{18}$F]FDG

The present inventors compared the imaging capabilities for melanoma and lung metastasis of the melanoma of [$^{18}$F]DMPY2 according to one embodiment of the present invention with the [$^{18}$F]FDG which has been used as a PET contrast agent for diagnosing cancer previously.

Particularly, melanoma xenograft model mice were prepared in the same manner as in Experimental Example 5, and then 7.4 MBq of [$^{18}$F]DMPY2 and [$^{18}$F]FDG were injected respectively, and systemic micro PET images were obtained at 1 hour after the injection.

In addition, after lung metastasis model mice were prepared in the same manner as in Experimental Example 6, 7.4 MBq of [$^{18}$F]DMPY2 and [$^{18}$F]FDG were injected, respectively, and systemic micro PET images were obtained at 1 hour after the injection.

Figure 7A:
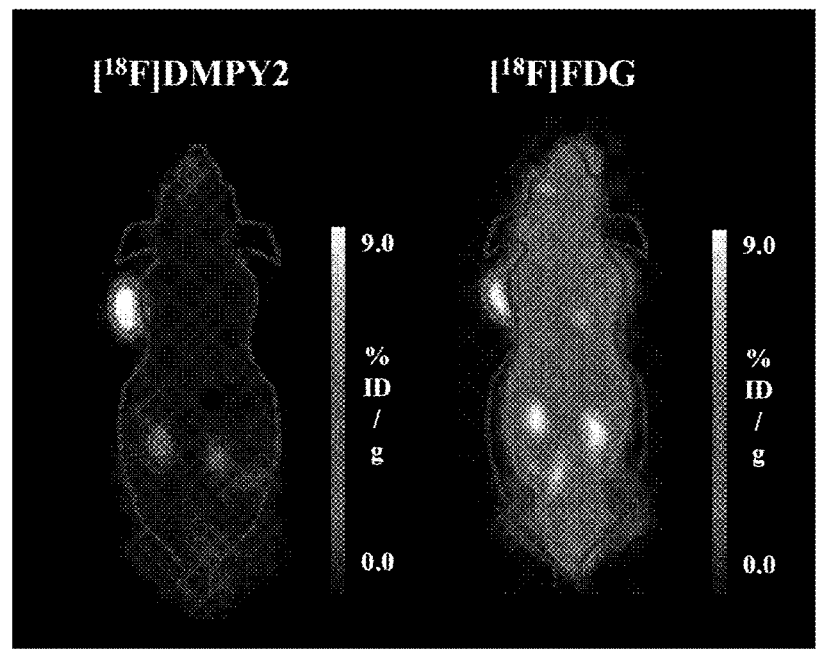
FIG. 7A is a series of micro PET images taken from B16F10 xenograft tumor model mice administered with [$^{18}$F]DMPY2 (left) and [$^{18}$F]FDG (right)
Figure 7B:
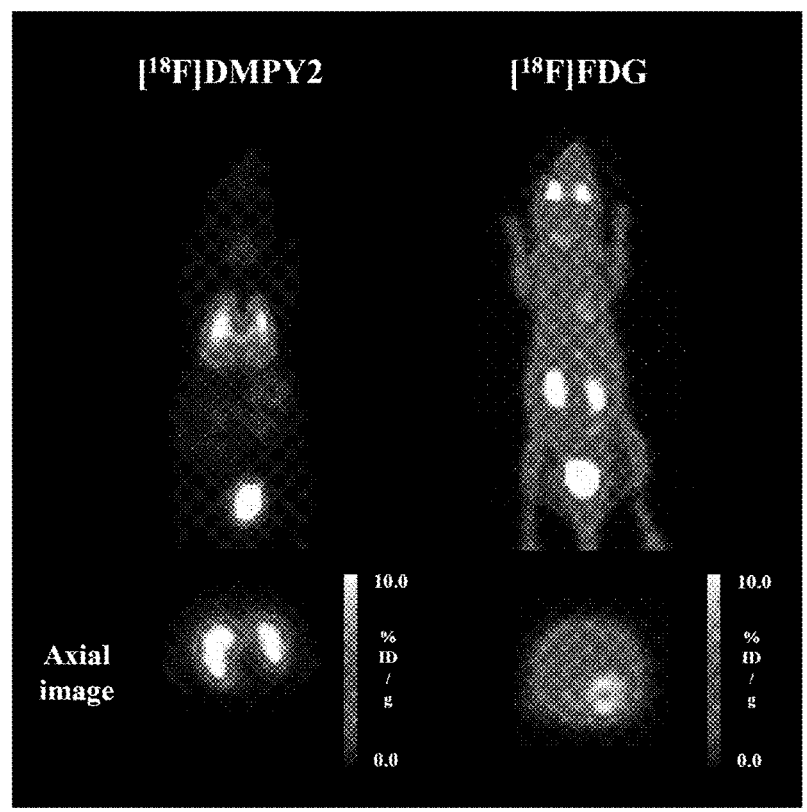
FIG. 7B is a series of micro PET images taken from lung metastasis model mice administered with [$^{18}$F]DMPY2 (left) and [$^{18}$F]FDG (right).

As a result, as shown in FIG. 7A, although [$^{18}$F]FDG showed a signal in the tumor tissue, background noise was widespread throughout the whole body and signals in other organs were similar to signals in the tumor tissue, [$^{18}$F] DMPY according to an embodiment of the present invention has a clear signal only in tumor tissue, and a signal to noise ratio is very high. In addition, as shown in FIG. 7B, in the case of [$^{18}$F]FDG, signals in other organs were found to be stronger than the lungs in which the metastasis occurred, and it was confirmed that diagnosing lung metastasis of melanoma with [$^{18}$F]FDG was unsuitable. On the other hand, [$^{18}$F]DMPY2 showed a very strong signal in the metastatic lung and little or no noise in other organs except bladder.

INDUSTRIAL APPLICABILITY

The radioactive compound according to one embodiment of the present invention can be very useful as a PET contrast agent for diagnosis of melanoma.

While the present invention has been described with reference to exemplary embodiments, it is to be understood that the invention is not limited to the disclosed exemplary embodiments, but, on the contrary, is intended to cover various modifications and equivalent arrangements included within the spirit and scope of the appended claims. Accordingly, the true scope of the present invention should be determined by the technical idea of the appended claims.

What is claimed is:

1. A radioactive compound or pharmaceutically acceptable salt thereof having the following formula:

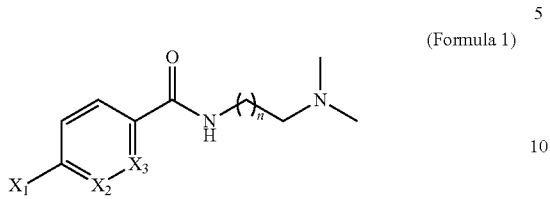

(Formula 1)

wherein $X_1$ is F or a chelator and a radioactive metal or a salt thereof selected from the group consisting of $^{68}$Ga, Al$^{18}$F, $^{62}$Cu and $^{64}$Cu;

$X_2$ is C and $X_3$ is N; and n is 1.

2. A contrast agent for positron emission tomography (PET) imaging comprising the radioactive compound or pharmaceutically acceptable salt thereof according to claim 1 as an active ingredient.

3. A method of diagnosing melanoma in a subject comprising administering the radioactive compound or pharmaceutically acceptable salt thereof according to claim 1, to the subject;

detecting radiation emitted from the radioactive compound which is accumulated and bound to melanoma tissue present in the subject; and diagnosing melanoma in the subject.

* * * * *